(12) United States Patent
Schwarz et al.

(10) Patent No.: US 9,750,437 B2
(45) Date of Patent: Sep. 5, 2017

(54) DETERMINATION OF NEURONAL ACTION POTENTIAL AMPLITUDE BASED ON MULTIDIMENSIONAL DIFFERENTIAL GEOMETRY

(71) Applicant: MED-EL Elektromedizinische Geraete GmbH, Innsbruck (AT)

(72) Inventors: Konrad Schwarz, Innsbruck (AT); Philipp Spitzer, Innsbruck (AT); Stefan Strahl, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 306 days.

(21) Appl. No.: 14/618,023

(22) Filed: Feb. 10, 2015

(65) Prior Publication Data
US 2015/0223734 A1 Aug. 13, 2015

Related U.S. Application Data

(60) Provisional application No. 61/938,312, filed on Feb. 11, 2014.

(51) Int. Cl.
*A61B 5/12* (2006.01)
*A61B 5/00* (2006.01)
(Continued)

(52) U.S. Cl.
CPC ............ *A61B 5/125* (2013.01); *A61B 5/686* (2013.01); *A61N 1/36032* (2013.01); *A61B 5/062* (2013.01); *A61B 5/063* (2013.01)

(58) Field of Classification Search
CPC .................... A61B 5/125; A61N 1/36032
See application file for complete search history.

(56) References Cited

U.S. PATENT DOCUMENTS 7,818,052 B2 10/2010 Litvak et al.
2005/0021207 A1 1/2005 Endo et al.
(Continued)

OTHER PUBLICATIONS

International Searching Authority, Authorized Officer Blaine R. Copenheaver, International Search Report and Written Opinion, PCT/US2015/015144, date of mailing May 15, 2015, 12 pages.

*Primary Examiner* — Michael C Stout
*Assistant Examiner* — Nicholas E Kolderman
(74) *Attorney, Agent, or Firm* — Sunstein Kann Murphy & Timbers LLP

(57) ABSTRACT

Arrangements are described for determining a physiological characteristic of the auditory pathway (as whole or selected parts such as an inner ear). Electrical stimulation pulses are delivered to inner ear neural tissue and corresponding tissue response signals are developed by measuring over time response of the auditory pathway to each electrical stimulation pulse, with each tissue response signal forming a response curve including at least one physiological landmark such as a local maximum and a local minimum. A multi-dimensional polynomial is fit over the tissue response signals, and calculation starting points are defined based on prominent physiologic landmarks such as a local maximum and a local minimum for one selected tissue response signal. A line of minimum principal curvature of the multi-dimensional polynomial over the plurality of tissue response signals that intersect the calculation starting points is calculated to determine a physiological characteristic of the auditory pathway.

27 Claims, 5 Drawing Sheets

(51) Int. Cl.
*A61N 1/36* (2006.01)
*A61B 5/06* (2006.01)

(56) References Cited

U.S. PATENT DOCUMENTS

| | | |
|---|---|---|
| 2009/0125081 A1 | 5/2009 | Spitzer et al. |
| 2010/0257128 A1 | 10/2010 | De Vries et al. |
| 2012/0109006 A1* | 5/2012 | James ................ A61N 1/36032 600/559 |
| 2012/0109274 A1 | 5/2012 | Simaan et al. |
| 2013/0303941 A1 | 11/2013 | Porges et al. |

* cited by examiner

DETERMINATION OF NEURONAL ACTION POTENTIAL AMPLITUDE BASED ON MULTIDIMENSIONAL DIFFERENTIAL GEOMETRY

This application claims priority from U.S. Provisional Patent Application 61/938,312, filed Feb. 11, 2014, which is incorporated herein by reference.

TECHNICAL FIELD

The present invention relates to detecting neuronal action potential signals from tissue responding to electrical stimulation signals, especially for hearing implant systems such as cochlear implant systems.

BACKGROUND ART

Most sounds are transmitted in a normal ear as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolus where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is associated with the cochlea 104, a cochlear implant with an implanted stimulation electrode can electrically stimulate auditory nerve tissue with small currents delivered by multiple electrode contacts distributed along the electrode. These electrodes may also be used for sensing neural tissue response signals, i.e. function as measurement electrodes.

In some cases, hearing impairment can be addressed by a cochlear implant (CI), a brainstem-, midbrain- or cortical implant that electrically stimulates auditory nerve tissue with small currents delivered by multiple electrode contacts distributed along an implant electrode. For cochlear implants, the electrode array is inserted into the cochlea. For brain-stem, midbrain and cortical implants, the electrode array is located in the auditory brainstem, midbrain or cortex, respectively.

FIG. 1 shows some components of a typical cochlear implant system where an external microphone provides an audio signal input to an external signal processor 111 which implements one of various known signal processing schemes. For example, signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, fine structure processing (FSP) and compressed analog (CA) signal processing.

The processed signal is converted by the external signal processor 111 into a digital data format, such as a sequence of data frames, for transmission by an external coil 107 into a receiving stimulator processor 108. Besides extracting the audio information, the receiver processor in the stimulator processor 108 may perform additional signal processing such as error correction, pulse formation, etc., and produces a stimulation pattern (based on the extracted audio information) that is sent through electrode lead 109 to an implanted electrode array 110. Typically, the electrode array 110 includes multiple stimulation contacts 112 on its surface that provide selective electrical stimulation of the cochlea 104.

To collect information about the electrode-nerve interface, a commonly used objective measurement is based on the measurement of Neural Action Potentials (NAPs) such as the electrically-evoked Compound Action Potential (eCAP), as described by Gantz et al., Intraoperative Measures of Electrically Evoked Auditory Nerve Compound Action Potentials, American Journal of Otology 15 (2):137-144 (1994), which is incorporated herein by reference. In this approach, the recording electrode is usually placed at the scala tympani of the inner ear. The overall response of the auditory nerve to an electrical stimulus is measured typically very close to the position of the nerve excitation. This neural response is caused by the super-position of single neural responses at the outside of the auditory nerve membranes.

FIG. 2 shows an example of measuring eCAP amplitude based solely on time since stimulation for a single response signal recording. The response signal is characterized by the amplitude between the minimum voltage (this peak is called typically N1) and the maximum voltage (peak is called typically P2), the so-called local extrema. These extrema among others represent the most prominent physiological landmarks of the ECAP signal. The amplitude of the eCAP at the measurement position is in most cases between approximately $10\mu V$ and $1800 \mu V$. One eCAP recording paradigm is a so-called "amplitude growth function," as described by Brown et al., Electrically Evoked Whole Nerve Action Potentials In Ineraid Cochlear Implant Users: Responses To Different Stimulating Electrode Configurations And Comparison To Psychophysical Responses, Journal of Speech and Hearing Research, vol. 39:453-467 (Jun. 1996), which is incorporated herein by reference. This function is the relation between the amplitude of the stimulation pulse and the peak-to-peak voltage of the eCAP.

In the past, relatively simple algorithms were used to determine the latencies of the extrema that represent physiological landmarks; for example, N1 or P2 from single recordings, which often produced physiologically unreasonable values that required manual correction of the determined latencies. Current state of the art methods are based on records of single pulses using only the time since stimulation as the basic factor for fitting functions providing the minima and maxima of the recorded signal. Standard sequences such as amplitude growth functions (AGF), recovery functions (RF) and spread of excitation functions (SoE) are especially affected by the lack of physiologic properties within the model, showing high variation in latencies of extrema or not detecting the extrema for single measurements due to signal artifacts. Artifacts, as understood in this context, are signal components in the recording not arising from physiologic effects that cannot be reduced by averaging multiple recordings.

Sophisticated algorithms are used to reduce the influence of signal artifacts from various sources; for example, alternating stimulation (Eisen M D, Franck K H: "Electrically Evoked Compound Action Potential Amplitude Growth Functions and HiResolution Programming Levels in Pediatric CII Implant Subjects." Ear & Hearing 2004, 25(6):528-538; incorporated herein by reference in its entirety), masker probe (Brown C, Abbas P, Gantz B: "Electrically evoked whole-nerve action potentials: data from human cochlear implant users." The Journal of the Acoustical Society of America 1990, 88(3):1385-1391; Miller C A, Abbas P J, Brown C J: An improved method of reducing stimulus artifact in the electrically evoked whole-nerve potential. Ear & Hearing 2000, 21(4):280-290; both incorporated herein by reference in their entirety), tri-phasic stimulation (Zimmerling M: "Messung des elektrisch evozierten Summenaktionspotentials des Hörnervs bei Patienten mit einem Cochlea-Implantat." In PhD thesis Universität Innsbruck, Institut für Angewandte Physik; 1999; Schoesser H, Zierhofer C, Hochmair E S. Measuring electrically evoked compound action potentials using triphasic pulses for the reduction of the residual stimulation artifact. In: Conference on implantable auditory prostheses; 2001; both of which are incorporated herein by reference in their entirety), scaled template (Miller C A, Abbas P J, Rubinstein J T, Robinson B, Matsuoka A, Woodworth G: Electrically evoked compound action potentials of guinea pig and cat: responses to monopolar, monophasic stimulation. Hearing Research 1998, 119(1-2):142-154; incorporated herein by reference in its entirety), or amplitude template (Brown, C. J.; Hughes, M. L.; Luk, B.; Abbas, P. J.; Wolaver, A. and Gervais, J. "The relationship between EAP and EABR thresholds and levels used to program the nucleus 24 speech processor: data from adults." Ear Hear, 21(2), pages 151-163, 2000; incorporated herein by reference in its entirety).

Even after applying various artifact reducing methods, the state-of-the art determination of extrema is not very robust (consistent for the whole sequence). The high failure rate and inaccuracy due to inaccurately detected extrema (and consequently eCAP-amplitudes) results in the use of other approaches to determine basic factors which are of interest for implant fitting such as the eCAP-threshold (SmartNRI as used by Advanced Bionics; Arnold, L. & Boyle, P. "SmartNRI: algorithm and mathematical basis." Proceedings of 8th EFAS Congress/10th Congress of the German Society of Audiology, 2007; (AutoNRT™ as used by Cochlear Ltd.; Botros, A.; van Dijk, B. & Killian, M. "AutoNRT™: An automated system that measures eCAP thresholds with the Nucleus(R) Freedom(tm) cochlear implant via machine intelligence" Artificial Intelligence in Medicine, 2007, 40, 15-28; which are incorporated herein by reference in their entirety).

Despite the weak performance of the fitting functions based only on time since stimulus to correctly determine the response signal amplitude, they still are used by filtering the basic recorded signal and subtracting a disturbing artifact. Standard evaluation procedures are highly affected by the resulting highly variable amplitude values and so need to be manually evaluated, or else specialized procedures can be used to determine subsequent values.

SUMMARY

Embodiments of the present invention are directed to arrangements for determining a physiological characteristic of auditory path (in whole or in part such as the inner ear). Electrical stimulation pulses are delivered to neural tissue of the auditory pathway (either as a whole or selected parts) and corresponding tissue response signals are developed by measuring over time response of the inner ear neural tissue to each electrical stimulation pulse, with each tissue response signal forming a response curve. A multi-dimensional polynomial is fit over the tissue response signals, and calculation starting points are defined for one selected tissue response signal. From the calculation starting points, a line of minimum principal curvature of the multi-dimensional polynomial over the plurality of tissue response signals that intersect the calculation starting points is calculated to determine a physiological characteristic of the inner ear.

The physiological characteristic may include an amplitude growth function where the multi-dimensional polynomial includes a post-stimulus time dimension and a stimulus intensity dimension. The physiological characteristic may include a tissue recovery function where the multi-dimensional polynomial includes a post-stimulus time dimension and an inter-stimulation pulse interval dimension. The physiological characteristic may include a spread of excitation function where the multi-dimensional polynomial includes a spatial distance dimension and an inter-stimulation pulse interval dimension. In specific embodiments, the multidimensional characteristic may include functions where the multi-dimensional polynomial includes different stimulation electrodes, different recording electrodes, different inter-phase gaps, various pulse shapes (e.g. biphasic, triphasic, etc.), different phase durations, various length of pulse trains (with or without amplitude modulation), measurements from different recording sessions over time and/or various masker-probe paradigms with or without changing ratios of masker/probe amplitudes. A skilled person can extend this list to further parameters that result in a continuous change of the physiologic response.

The line of minimum principal curvature may be calculated iteratively. Some embodiments may also output the closeness of the multi-dimensional fit as a function of the carrier of the measurements. The multi-dimensional polynomial may have a fixed degree or it may be a variable degree polynomial. The tissue response signals may specifically include electrically evoked compound action potential (eCAP) signals.

DETAILED DESCRIPTION

Figure 3:
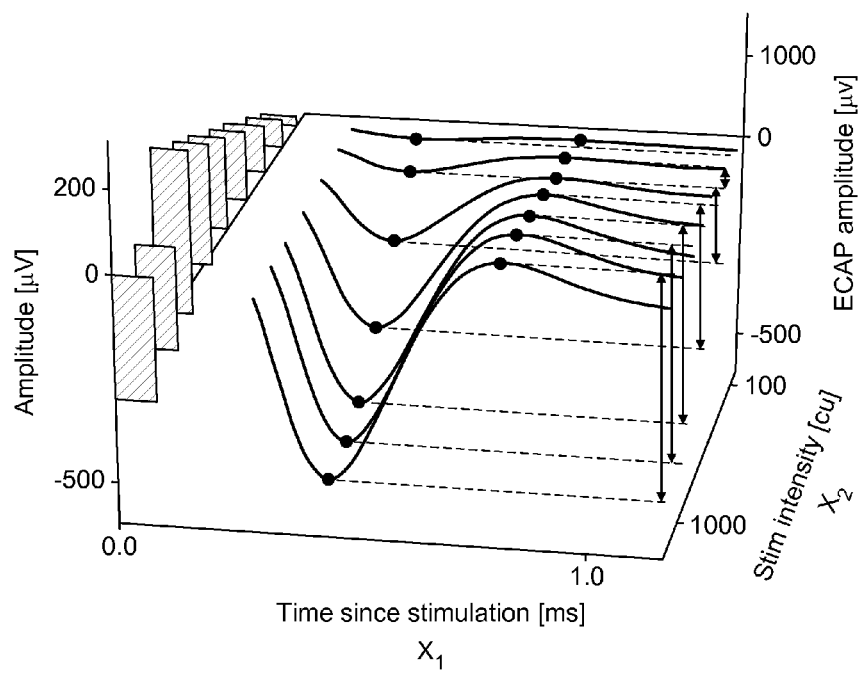
FIG. 3 shows an example of using multiple response signal recordings to measure eCAP amplitude as a function of both time since stimulus and stimulation intensity.

Embodiments of the present invention are based on a fitting of a multi-dimensional polynomial over multiple measurement tissue response signals. For example, besides time after delivery of the electrical stimulation pulse, the multi-dimensional polynomial fitting function also may reflect stimulation intensity (amplitude growth function, AGF) and/or time difference of a masking pulse (recovery functions, RF). FIG. 3 shows an example of using multiple response signal recordings to measure eCAP amplitude as a function of both time since stimulus and stimulation intensity. It can be seen that the eCAP amplitude increases with stimulus intensity. In some specific embodiments, other additional factors can be incorporated into the fitting function (e.g. pairs of recording electrodes) by adding and/or replacing a corresponding dimension. Based on such multi-dimensional fitting function, the analysis of the resulting principal curvature yields a robust determination of the physiological landmarks of the signal such as extrema, and thereby the neuronal action potentials that are present within sequences of tissue response signals.

Figure 1:
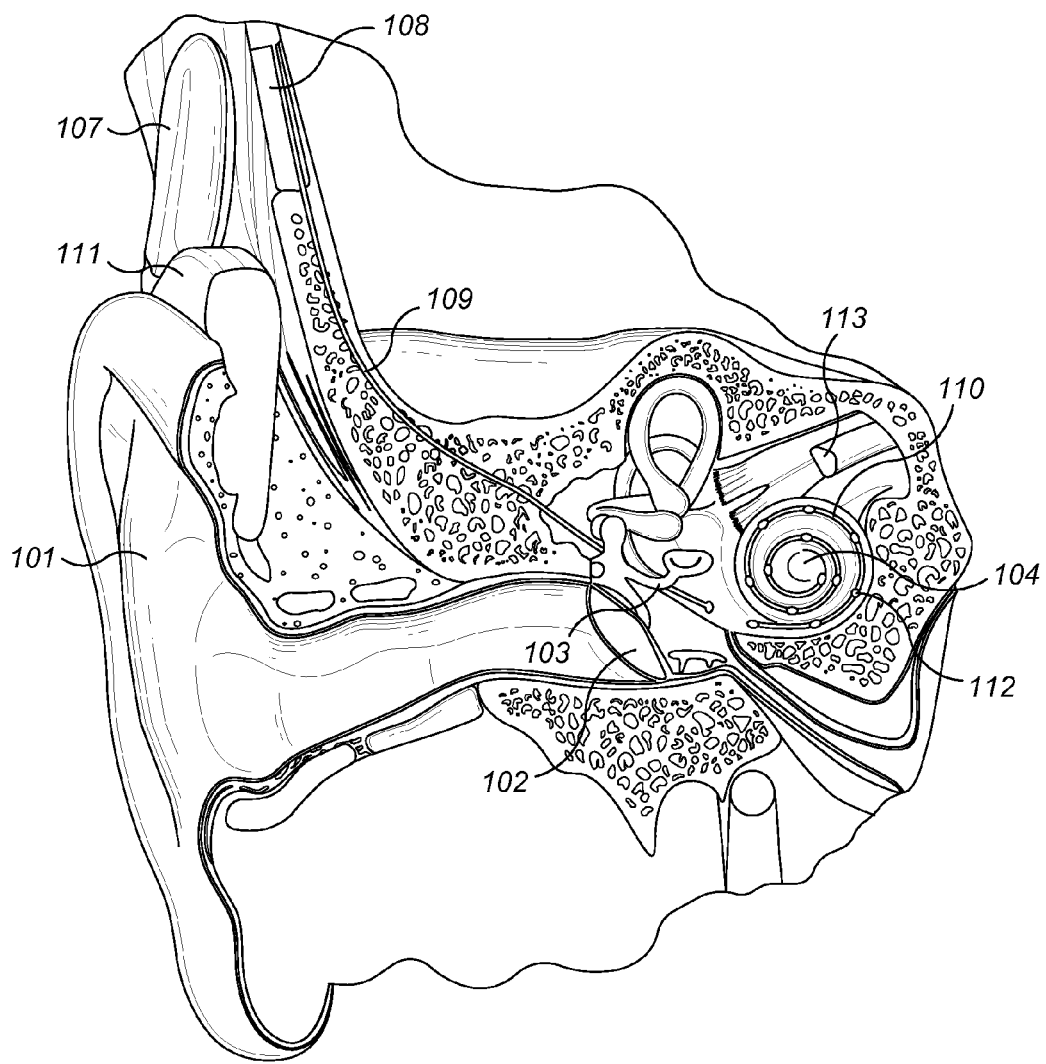
FIG. 1 shows anatomical structures of a human ear having a cochlear implant system.
Figure 2:
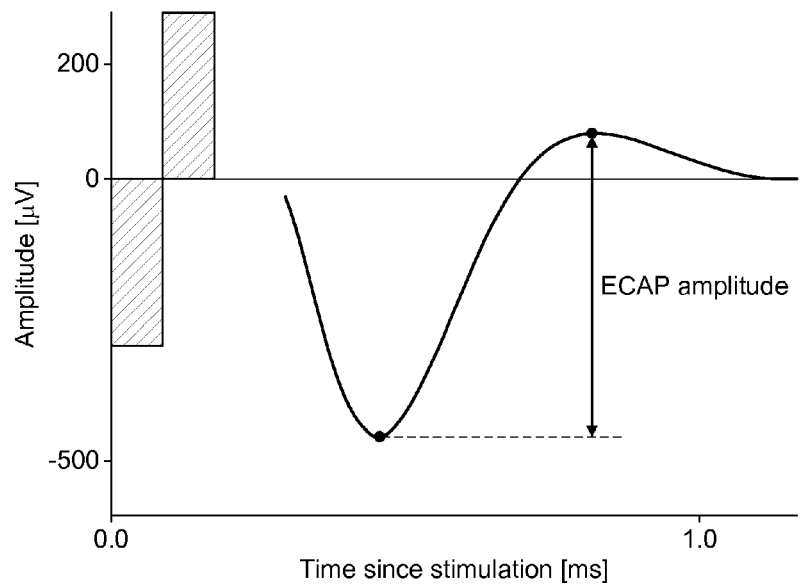
FIG. 2 shows an example of measuring eCAP amplitude based solely on time since stimulation for a single response signal recording.
Figure 4:
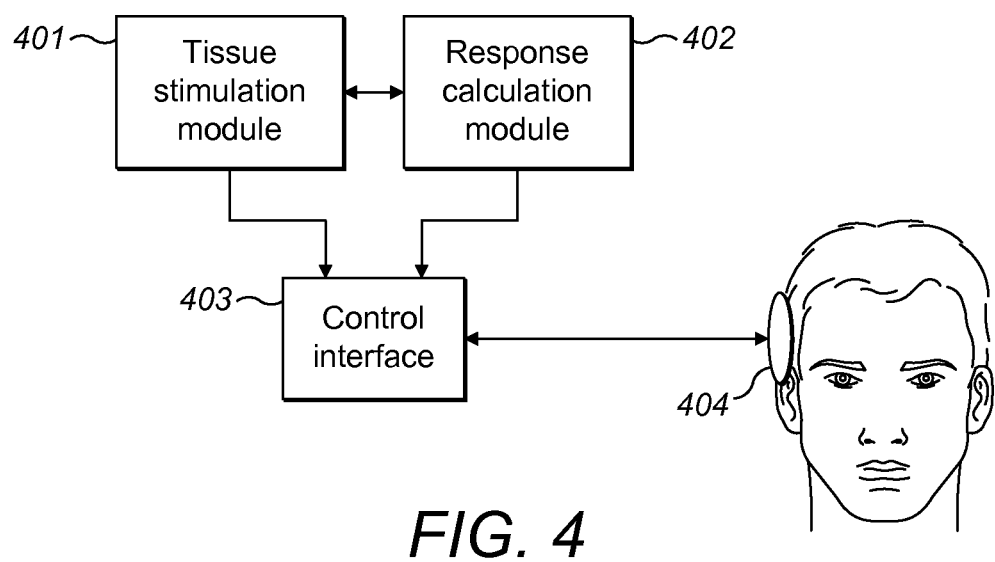
FIG. 4 shows various components in a system for measuring neural action potential (NAP) signals from tissue responding to electrical stimulation signals according to one specific embodiment of the present invention.
Figure 5:
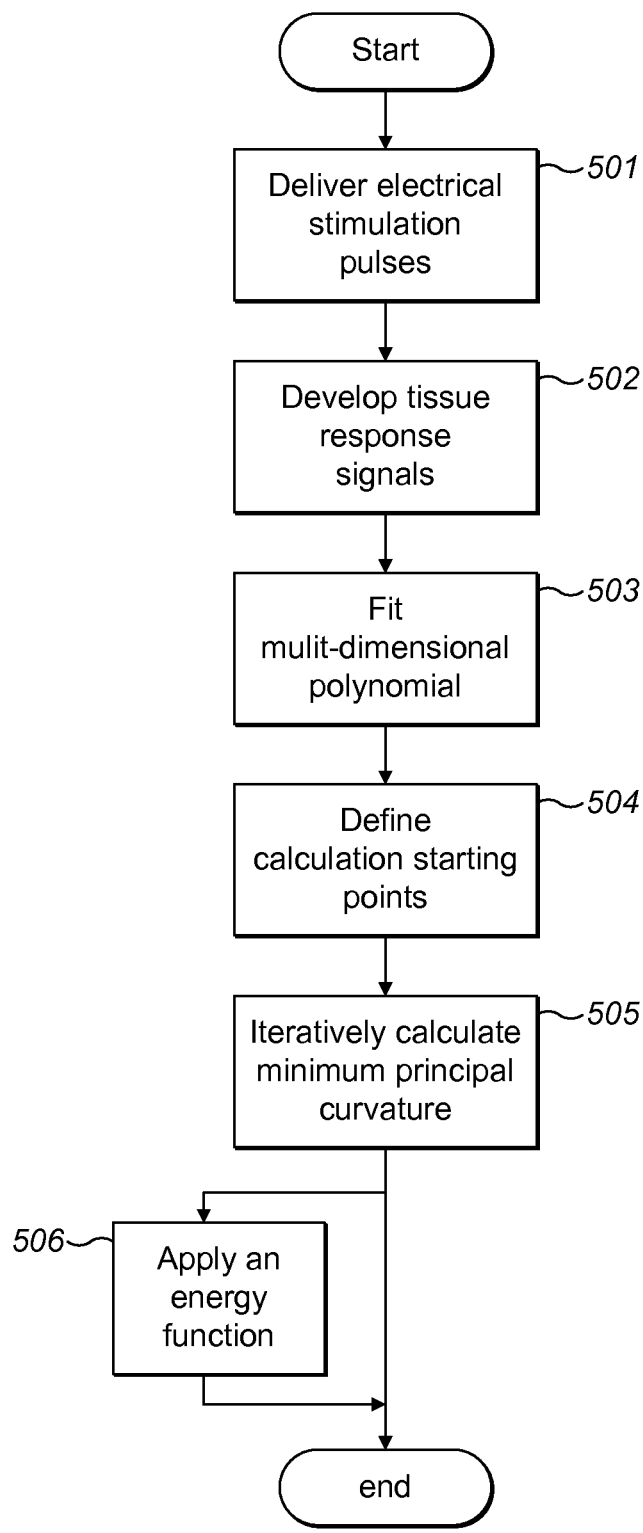
FIG. 5 shows the functional steps in a method of measuring neural action potential (NAP) signals from tissue responding to electrical stimulation signals according to one specific embodiment of the present invention.

FIG. 4 shows various components in a system for measuring neural action potential signals and FIG. 5 shows the functional steps in a method of measuring neural action potential signals from tissue responding to electrical stimulation signals according to embodiments of the present invention. A tissue stimulation module 401 generates electrical stimulation pulses that a control interface module 403 sends to a cochlear implant 404, which delivers the stimulation pulses (e.g., bi-phasic or tri-phasic stimulation pulses) to neural tissue in the auditory pathway (in whole or in selected part such as the inner ear, step 501. In specific embodiments, the intensity of the electrical stimulation pulses may be varied; for example, increased or decreased for each measurement, and similarly the time between each electrical stimulation pulse may be either some predefined set interval or it may be varied for each measurement. In response to the delivered stimulation pulses, corresponding tissue response signals are developed by measuring the response over time of the auditory pathway neural tissue to each electrical stimulation pulse, step 502. This is performed by sensing electrodes (e.g., cochlear implant electrode contacts) adjacent to the neural tissue. Each tissue response signal that forms a response curve including at least one local maximum and at least one local minimum (see FIG. 2) is selected. These are sensed and may be averaged and delivered via the control interface module 403 to a response calculation module 402.

The response calculation module 402 fits a multi-dimensional polynomial over the tissue response signals, step 503, and defines calculation starting points for the physiological landmarks—for extrema they are based on a local maximum and a local minimum for one selected tissue response signal, step 504. In a given set of multiple tissue response signals there may be some individual recordings that do not have a well-defined physiological landmarks such as local maxima and/or minima. Clearly such signals are not suitable to be selected for use as calculation starting points, and in specific embodiments, such outlier signals may or may not be included in the subsequent calculations. A given tissue response signal with the most prominent landmark e.g. lowest minimum and/or highest maximum may be selected as the basis for the calculation starting points. Or a given tissue response signal with the greatest difference between the minimum N1 and maximum P2 may be selected. Or tissue response signals with the strongest stimulation impulse (e.g., for amplitude growth function) or maximal time difference between a masker pulse and a probe pulse (recovery function).

From the calculation starting points, the response calculation module 402 iteratively calculates a line of minimum principal curvature of the multi-dimensional polynomial over the plurality of tissue response signals to determine a physiological characteristic of the inner ear, step 505. For example, the physiological characteristic may include an amplitude growth function where the multi-dimensional polynomial includes a post-stimulus time dimension and a stimulus intensity dimension, a tissue recovery function where the multi-dimensional polynomial includes a post-stimulus time dimension and an inter-stimulation pulse interval dimension, and/or an spread of excitation function where the multi-dimensional polynomial includes a spatial distance dimension and an inter-stimulation pulse interval dimension. Optionally, once the line of minimum principle curvature has been calculated, a specific embodiment may further apply an energy function, step 506, as described in further detail below.

The various fitting factors such as time since stimulation [ms], the stimulation intensity [μA], the time between first and second stimulus [ms], spatial distance between stimulation and recording electrodes, or any factor affecting a continuous change of the eCAP signal can be regarded as $x_1$, $x_2$, ... $x_n$ respectively. The measured tissue response signal [μV] is denoted as y, where $x_1, x_2, \ldots y \in \mathbb{R}$. The fitting function is then modeled as a multi-dimensional polynomial where $n \in \mathbb{N}$ denotes the number of modeled factors, $d_i \in \mathbb{N}$ is the degree of the polynomial along dimension i, and $a_{(i_1, i_2, \ldots, i_n)} \in \mathbb{R}$ are the corresponding weighting parameters:

$$P(x_1, x_2, \ldots, x_n) = \sum_{i_1=0}^{d_1} \left( \sum_{i_2=0}^{d_2} \ldots \left( \sum_{i_n=0}^{d_n} a_{(i_1, i_2, \ldots, i_n)} * \prod_{j=1}^{n} x_j^{i_j} \right) \ldots \right)$$

Polynomials function evaluations can be calculated quickly, and partial derivations (and other further mathematical processes) can be calculated analytically. The number of the different weighting parameters $a_{(i_1, i_2, \ldots, i_n)} \in \mathbb{R}$ depends on the specific degree of the polynomial $d_1, \ldots, d_n \in \mathbb{N}$. The multi-dimensional polynomial may have a fixed degree or it may be a variable degree polynomial. And the degree may be different for different dimensions. For example, the degree in the $x_1$ direction may be fixed at 6 while the degree in the $x_2$ direction may be fixed at 3. The degree may be fixed in one or more dimensions and variable in the one or more other dimensions. Fitting functions based only on time after stimulus ($x_1$) are already known, so the degree for this influencing factor can be fixed as used in standard methods within a typical range: $10 < d_1 < 20$. The degree of the other chosen influencing factors $d_2, \ldots, d_n$, can be kept minimal and can be derived by successively increasing the degree [$d_j$] for single factors and if the additional weighting parameters are significantly different from zero, that weighting parameter degree can be increased further. With a fixed set of weighting parameters and with each parameter appearing only linearly, the weighting parameters can be estimated by fast analytical linear regression models based on Vandermonde matrices. The initial estimate of the polynomial degree may start at a given fixed value such as 3, and the degree can then be increased and the fitting repeated with each such increase. If additional weighting parameters of the polynomial are close to zero, then no further degree increase may be needed. Increasing the degree of the polynomial may depend on a stability index along the considered dimension, which can be obtained as a by-product from the fitting. Partial derivations can be analytically given and deduced values can be determined based on analytical expressions.

For artifact-free tissue response signals, the extrema as most prominent physiological landmarks of the eCAP response due to the time after stimulus can be easily found using the first partial derivative of the amplitude function $\partial/\partial x_1 P(x_1, x_2, \ldots, x_n)$. If there are artifacts for individual tissue response signals, the multi-dimensional fit would inherently enable interpolation of the tissue response signals. Even when the signal extrema are completely hidden by the artifacts, the inner geometry of a multi-dimensional fit can be used to determine the extrema.

Figure 6:
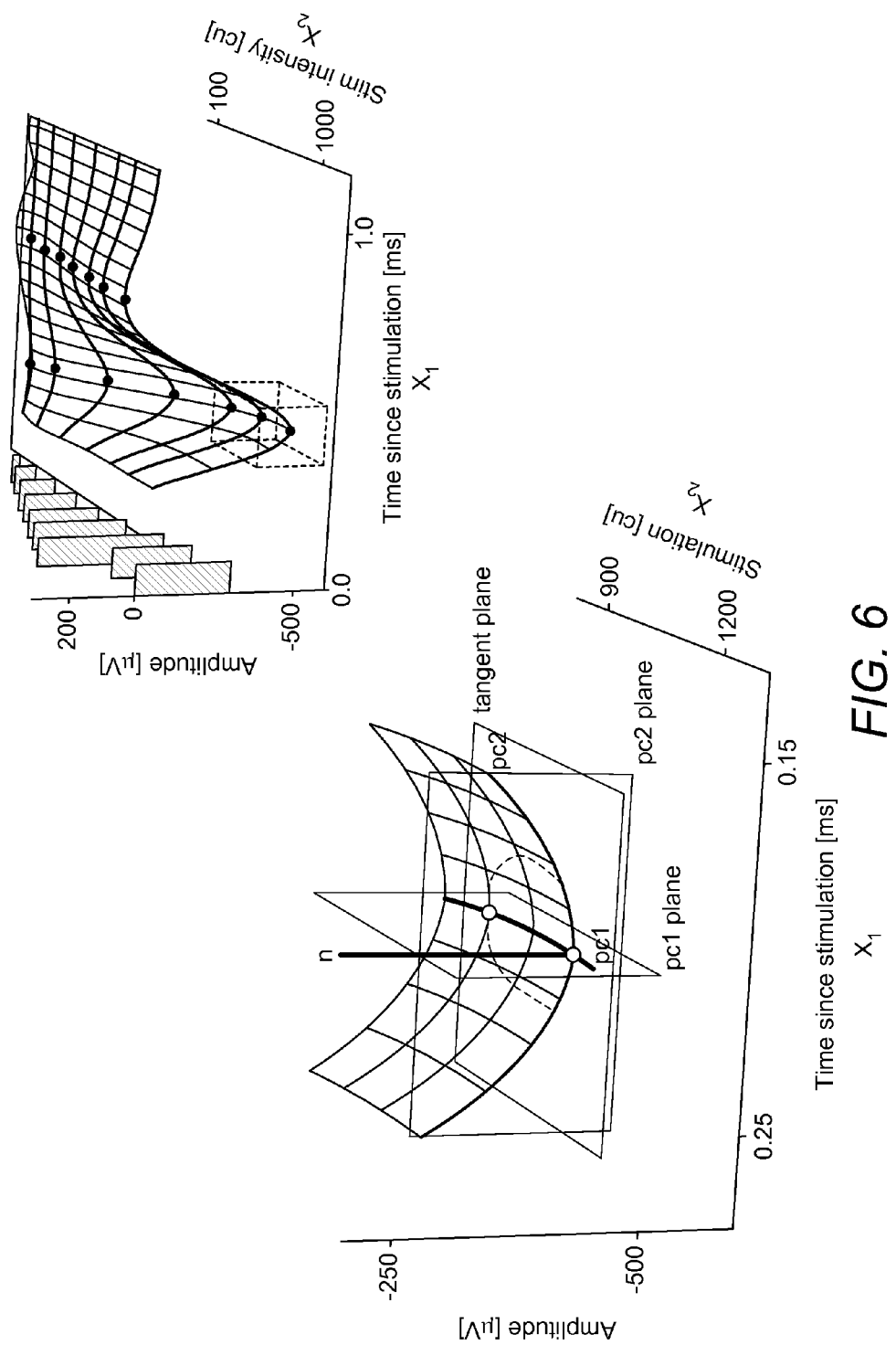
FIG. 6 shows an example of determining local extrema using principal curvature according to an embodiment of the present invention.

For example, as shown in FIG. 6, for given sequences of stimuli, the amplitude function can be projected in a three dimensional space (by fixing additional factors) and thus be considered as a surface embedded in $\mathbb{R}^3$. For such a surface, the direction of the principal curvatures can be calculated analytically from $P(x_1, x_2, \ldots, x_n)$ for single points (with fast computation times), and thus for given calculation starting points (e.g., for AGFs, the greatest stimulation intensity minimum N1 of a single measurement) and small steps along one dimension (e.g. stimulation intensity [cu] for AGFs), the principal curvatures are given by iterative formulas. Because of the minimal curvature, the calculated direction yields to a line along the curve where the remaining minima N1 or maxima P2 are located for other stimulus intensities. Since the principal curvatures are within planes through the normal vector at a single point, this determination of extrema is much more robust for the case where linear signal artifacts cannot be completely filtered (as is typically the case for stimulation artifacts). In the small picture in the upper right corner of FIG. 6, the eCAP answer is shown modeled as function depending on time since stimulus and stimulation intensity. In the main panel of FIG. 6, a sketch of the mathematical definition of extrema determination is outlined: n denotes the normal vector, pc1 respectively pc2 the minimal and maximal principal curvatures. A change in amplitude depending on a change of the influencing factors can be described in a single point (here in N1 at stimulation intensity 1200 [cu]) by the first partial derivation of the amplitude function, or alternatively by regarding the principal curvatures. The dotted line is showing the intercept of the amplitude function with a plane parallel to the tangent plane, reflecting roughly the constraints between curvature ("second partial derivation") and change in amplitude. The two curves called minimal and maximal "principal curvatures" are intersect lines between planes through the normal vector and the amplitude function where the curvature of the resulting curves is at the minimal respectively maximal possible value.

So a specific algorithm for determining a curve where the extrema are located is given by a principal curvature which can be calculated as follows. First define a set of calculation starting points (E.g. extrema due to the first partial derivative of the amplitude function $\partial/\partial x_1 P(x_1, x_2, \ldots, x_d)$). Beginning with the defined calculation starting point, make a step due to the direction of the minimal principal curvature until the entire range of the second factor of interest (for AGFs, stimulation intensity, for RFs, time between masker and probe pulse) is processed. This may be done for one selected calculation starting point or repeated for each calculation starting point and a curve or a set of curves is derived for $(x_1, x_2, P(x_1, x_2, \ldots, x_n))$ with $x_2, \ldots, x_n \in \mathbb{R}$ fixed and $a < x_2 < b$; $a, b, x_2 \in \mathbb{R}$ and corresponding $x_1 \in \mathbb{R}$. In the latter case out of the resulting set of defined curves, the optimal curves for physiological landmarks such as N1 and P2 are selected.

Once the line of minimal principal curvature has been determined for each calculation starting point, some embodiments may further apply an energy function to the resulting set of defined curves. In this context, the higher the energy of one of the individual curves in the set of curves, the more likely it is that this curve is finally selected. The energy may further indicate the quality of how well the selected tissue response signal is representative for the physiologic characteristic. For example, if the energy is above a certain threshold, the tissue response signal is considered of good quality. The threshold may be fixed, for example heuristically determined, or may depend on response amplitude and/or signal-to-noise ratio and/or a statistical measure of the fitting. The energy function may include one or more components of stimulation pulse intensity ($\epsilon_{int}$), measurement point response amplitude ($\epsilon_{ampl}$), difference to physiological landmarks such as extrema values ($\epsilon_{ext}$) and/or difference to average or mean values ($\epsilon_{vals}$). Any of these components may be normalized. The energy function may for example be derived by multiplication of the one or more derived components.

$$\varepsilon_{curve} = \sum_{j \in \{x_2\}} \varepsilon_{vals,j} \cdot \varepsilon_{ext,j} \cdot \varepsilon_{int,j} \cdot \varepsilon_{ampl,j}$$

For an entire set of calculation starting points, the tissue response signal may be selected as representative of the physiologic characteristic based on an energy function. The selected tissue response signal may the one with maximum energy. In a further embodiment the tissue response signal may be optimized by means of a least mean square (LMS) fit over the resulting set of defined curves. In such an LMS fit, the standard deviations associated with each tissue response signal may vary; for example, as a function of the difference between the minimum and the maximum where a large difference indicates a reliable measurement with little measurement error (small standard deviation).

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments also can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A fitting system including at least one hardware-implemented processor for fitting a cochlear implant having an implanted electrode array with a plurality of stimulation electrodes to an implanted patient based on determining a physiological characteristic of the auditory pathway in the implanted patient, the system comprising:
    a tissue stimulation module in communication with the cochlear implant via a control interface and configured to generate a plurality of electrical stimulation pulses to the one or more stimulation electrodes for delivery to auditory neural tissue of the inner ear of the implanted patient;
    one or more response measurement electrodes on the implanted electrode array configured to measure neural response over time of the auditory pathway to the electrical stimulation pulses to develop a plurality of tissue response signals, wherein each tissue response signal forms a response curve; and
    a response calculation module including at least one hardware-implemented processor and coupled to the response measurement electrodes to receive the tissue response signals and configured to determine the physiological characteristic by:
        i. fitting a multi-dimensional polynomial over the plurality of tissue response signals,
        ii. defining calculation starting points for one selected tissue response signal,
        iii. calculating a line of minimum principal curvature of the multi-dimensional polynomial over the plurality of tissue response signals that intersect the calculation starting points to determine the physiological characteristic of the auditory pathway, and
        iv. providing fitting instructions via the control interface to the cochlear implant based on the physiological characteristic of the auditory pathway to fit operation of the cochlear implant to the implanted patient.

2. The system according to claim 1, wherein the physiological characteristic includes an amplitude growth function.

3. The system according to claim 2, wherein the multi-dimensional polynomial includes a post-stimulus time dimension and a stimulus intensity dimension.

4. The system according to claim 1, wherein the physiological characteristic includes a tissue recovery function.

5. The system according to claim 4, wherein the multi-dimensional polynomial includes a post-stimulus time dimension and an inter-stimulation pulse interval dimension.

6. The system according to claim 1, wherein the physiological characteristic includes a spread of excitation function.

7. The system according to claim 6, wherein the multi-dimensional polynomial includes a spatial distance dimension and an inter-stimulation pulse interval dimension.

8. The system according to claim 1, wherein the physiological characteristic includes a physiological characteristic resulting in a continuous function of the signal selected from the group of an amplitude growth function, a tissue recovery function, and a spread of excitation function.

9. The system according to claim 1, wherein the response calculation module uses a local maximum and a local minimum of the one selected tissue response signal to define the calculation starting points.

10. The system according to claim 1, wherein the response calculation module calculates the line of minimum principal curvature iteratively.

11. The system according to claim 1, wherein the response calculation module further outputs multi-dimensional fit closeness as a function of the carrier of the measurements.

12. The system according to claim 1, wherein the multi-dimensional polynomial has a fixed degree.

13. The system according to claim 1, wherein the multi-dimensional polynomial has a variable degree.

14. The system according to claim 1, wherein the tissue response signals include electrically evoked compound action potential (eCAP) signals.

15. A computer implemented method using at least one hardware-implemented processor for fitting a cochlear implant having an implanted electrode array with a plurality of stimulation electrodes to an implanted patient based on determining a physiological characteristic of the auditory pathway in the implanted patient, the method comprising:
    delivering a plurality of electrical stimulation pulses from a tissue stimulation module via a control interface to the stimulation electrodes to stimulate inner ear neural tissue;
    developing a plurality of tissue response signals with one or more response measurement electrodes on the implanted electrode array by measuring over time a corresponding neural response of the inner ear neural tissue to each electrical stimulation pulse, wherein each tissue response signal forms a response curve;
    using a response calculation module including at least one hardware-implemented processor to receive the plurality of tissue response signals and determine the physiological characteristic by:
        i. fitting a multi-dimensional polynomial over the plurality of tissue response signals;
        ii. defining calculation starting points for one selected tissue response signal;
        iii. calculating a line of minimum principal curvature of the multi-dimensional polynomial over the plurality of tissue response signals that intersect the calculation starting points to determine the physiological characteristic of the auditory pathway; and
        iv. providing fitting instructions via the control interface to the cochlear implant based on the physiological characteristic of the auditory pathway to fit operation of the cochlear implant to the implanted patient.

16. The method according to claim 15, wherein the physiological characteristic includes an amplitude growth function.

17. The method according to claim 16, wherein the multi-dimensional polynomial includes a post-stimulus time dimension and a stimulus intensity dimension.

18. The method according to claim 15, wherein the physiological characteristic includes a tissue recovery function.

19. The method according to claim 18, wherein the multi-dimensional polynomial includes a post-stimulus time dimension and an inter-stimulation pulse interval dimension.

20. The method according to claim 15, wherein the physiological characteristic includes a spread of excitation function.

21. The method according to claim 15, wherein the physiological characteristic includes a physiological characteristic resulting in a continuous function of the signal selected from the group of an amplitude growth function, a tissue recovery function, and a spread of excitation function.

22. The method according to claim 21, wherein the multi-dimensional polynomial includes a spatial distance dimension and an inter-stimulation pulse interval dimension.

23. The method according to claim 15, wherein the line of minimum principal curvature is calculated iteratively.

24. The method according to claim 15, further comprising:
outputting multi-dimensional fit closeness as a function of the carrier of the measurements.

25. The method according to claim 15, wherein the multi-dimensional polynomial has a fixed degree.

26. The method according to claim 15, wherein the multi-dimensional polynomial has a variable degree.

27. The method according to claim 15, wherein the tissue response signals include electrically evoked compound action potential (eCAP) signals.

* * * * *